United States Patent [19]
Gregory et al.

[11] Patent Number: 5,671,314
[45] Date of Patent: Sep. 23, 1997

[54] ILLUMINATOR DEVICES FOR ULTRAVIOLET LIGHT DELIVERY AND METHODS OF MAKING SAME

[75] Inventors: Kenton W. Gregory, West Linn; Hanqun Shanqquan; Thomas E. Haw, both of Portland, all of Oreg.

[73] Assignee: Sisters of Prividence in Oregon, Portland, Oreg.

[21] Appl. No.: 2,865

[22] Filed: Jan. 15, 1993

[51] Int. Cl.⁶ .................................................. G02B 6/22
[52] U.S. Cl. ........................ 385/128; 385/901; 385/31; 385/127; 362/32
[58] Field of Search ........................ 385/128, 902, 385/31, 36, 901, 126, 127; 362/32

[56] References Cited

U.S. PATENT DOCUMENTS

| | | | |
|---|---|---|---|
| 5,074,632 | 12/1991 | Potter | 385/31 |
| 5,119,461 | 6/1992 | Beyer et al. | 385/902 X |
| 5,337,381 | 8/1994 | Biswas et al. | 385/36 |
| 5,363,458 | 11/1994 | Pan et al. | 385/31 |
| 5,373,571 | 12/1994 | Reid et al. | 385/31 |
| 5,530,780 | 6/1996 | Ohsawa | 385/31 |

*Primary Examiner*—Phan T. H. Palmer
*Attorney, Agent, or Firm*—Nixon & Vanderhye, P.C.

[57] ABSTRACT

Illumination devices (20, 20', 20", 20'") for delivering ultraviolet light to an in vivo treatment site comprise an optical fiber (22) having an illumination window (40, 40', 40", 40'"). A circumferential contour (46, 46', 46", 46'") of the core is shaped along the illumination window so that, for an internally reflected ray travelling in the core, the internally reflected ray has differing angles of incidences along the illumination window. In addition, the contour of the circumferential core causes rays travelling parallel to a major axis of the optical fiber to strike the core-scattering layer interface, thereby resulting in greater irradiance. In one embodiment, in the illumination window (40') a circumferential contour (46') of the core is shaped by etching to have an essentially semi-conical shape. In another embodiment, in the illumination window (40") the circumferential contour of the core has a plurality of circumferential segments (46a", 46b", 46c"), one of which has an essentially semi-conical shape and another of which has a reduced radius annular shape. In another embodiment, a reflective surface (60) is formed at a distal end of the optical fiber. An optical scattering material (48, 48', 48") is formed over the fiber core in the illumination window. The optical scattering material is preferably an admixture of optical epoxy and $Al_2O_3$.

42 Claims, 10 Drawing Sheets

ILLUMINATOR DEVICES FOR ULTRAVIOLET LIGHT DELIVERY AND METHODS OF MAKING SAME

BACKGROUND

1. Field of Invention

This invention pertains to devices for delivering ultraviolet light in connection with photochemotherapeutic treatments, including illuminators for use with angioplasty balloons, and methods of making such devices.

2. Prior Art and Other Considerations

In in vivo photochemotherapeutic treatments, a patient takes an inert photo-ignited drug. Once the drug is in the body, the drug can be "turned on" by an irradiation of laser energy (ultraviolet light), thereby selectively creating a therapeutic photochemical reaction only at the site of the irradiation.

Photochemotherapeutic treatments are particularly suited to vascular procedures. When used with the proper drugs, the selective application of the ultraviolet light creates a photochemical reaction which inhibits or impedes the restenosis which typically occurs as a result of vascular injury, vascular surgery, or angioplasty (e.g., balloon angioplasty, laser angioplasty, or mechanical angioplasty). See, for example, U.S. patent application Ser. No. 07/781,996, filed Oct. 23, 1991, now abandonment by Kenton W. Gregory and R. Rox Anderson, entitled "Laser-Based Inhibition of Smooth Muscle Cell Hyperproliferation", which is incorporated herein by reference, and U.S. Pat. No. 5,116,864 issued to March et al.

In such vascular photochemotherapeutic procedures, the laser energy is preferably emitted in a circumferential, cylindrical irradiation pattern from an optical fiber that terminates in a central diffusing tip of an angioplasty balloon. Currently the typical optical fiber diffusing tips for photochemotherapeutic treatments are made by removing a cladding of the optical fiber (over a desired length from the tip of the fiber) and replacing the cladding with a thin layer of optical scattering materials. Alternatively, a diffuser is attached to a distal end of the optical fiber.

Unfortunately, the current methods for making illuminator tips are rather complex, particularly when the configuration of the tip is dictated by constraints (e.g., small diameter) associated with a balloon with which the tip is to operate.

It is required that illumination devices utilized for vascular photochemotherapeutic procedures yield a nearly uniform cylindrical pattern of irradiation. However, the more miniature the device, the more the difficulty that is encountered in obtaining irradiation uniformity.

Accordingly, it is an object of the present invention to provide an illuminator tip which provides relatively uniform irradiation for photochemotherapeutic procedures.

An advantage of the present invention is the provision of fabrication methods for making embodiments of illuminator tips.

SUMMARY

Illumination devices for delivering ultraviolet light to an in vivo treatment site comprise an optical fiber having an illumination window. The illumination window is formed by removing buffer material and cladding material from a core of a silica optical fiber along a predetermined length thereof, treating the core along the predetermined length to specially configure the core, and applying an optical scattering layer over the specially configured core.

Essentially uniform cylindrical irradiation is desired for in vivo photochemotherapeutic treatments. The illumination devices of the present invention achieve uniform cylindrical irradiation by using the illumination window to redistribute the light emanating from the fiber core. In particular, a circumferential contour of the core is shaped along the illumination window so that, for an internally reflected ray travelling in the core, the internally reflected ray has differing angles of incidences along the illumination window. In addition, the contour of the circumferential core causes rays travelling parallel to a major axis of the optical fiber to strike the core-scattering layer interface, thereby resulting in greater irradiance.

In one embodiment, in the illumination window a circumferential contour of the core is shaped by etching to have an essentially semi-conical or truncated conical shape. In this embodiment, a portion of the core has the shape of a truncated cone along the illumination window. The truncated conical core has an internal planar conical angle $\alpha$. An internally reflected ray which has a first angle of incidence $\theta_1$ at a first point of reflection along the illumination window and a plurality N of further points of subsequent reflection along the predetermined length, will have an interior angle of total reflection of $2(\theta_i-(N-1)\alpha)$ for the subsequent points of internal reflection in the illumination window.

In another embodiment, in the illumination window the circumferential contour of the core has a modified conical or bi-tapered contour including a plurality of circumferential contour segments. A first of the circumferential contour segments has an essentially semi-conical shape. Light behaves in this semi-conical contour segment much in the manner as with the illumination window of the previous embodiment. A second of the circumferential contour segments, which is upstream from the first segment, has a reduced radius annular shape, thereby enhancing irradiation from an upstream portion of the illumination window.

In all embodiments, an optical scattering material is formed over the fiber core in the illumination window. The optical scattering material is preferably an admixture of optical epoxy and $Al_2O_3$.

Methods for forming the embodiments of the illumination devices are also disclosed.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating the principles of the invention.

FIGS. 3A–3G are schematic cross-sectional views showing stages of preparation of an illuminator device according to the embodiment of FIG. 1B.

FIGS. 4A–4C are schematic cross-sectional views showing stages of preparation of an illuminator device according to the embodiment of FIG. 1C.

DETAILED DESCRIPTION OF THE DRAWINGS

FIGS. 1A, 1B, 1C, and 1D are cross-sectional schematic views of illuminator devices 20, 20', 20", and 20'" according to four differing embodiments of the invention. Identical reference numerals are employed to reference similar structure for the embodiments of FIGS. 1A, 1B, 1C, and 1D.

The illuminator devices 20, 20', 20", and 20'" each comprise an optical fiber 22 having an acceptance end 24, a distal end 26, and a major axis 28. As used herein, the acceptance end 24 is sometimes referred to as the "upstream" end, and the distal end is sometimes referred to as the "downstream" end. Reference herein to "upstream" and "downstream" directions is similarly understood with respect to the acceptance end 24 and the distal end 26.

The optical fiber 22 has a central core 30 which (unless otherwise noted) has a radius R. As used herein, it should be understood that the radius of the core along any point of the length of the fiber is taken in a plane which is perpendicular to the major axis 28.

The core 30 is surrounded by an circumferential cladding material 32. The cladding material 32 is, in turn, surrounded by a circumferential buffer material 34.

The acceptance end 24 of the optical fiber 22 is prepared to have a laser beam incident thereon (as hereinafter described) through coupling optics. The opposite or distal end 26 of the optical fiber 22 is polished and coated with an optically opaque epoxy 36.

The illuminator devices 20, 20', 20", and 20'" have illumination windows 40, 40', 40", and 40'" provided thereon (see respective FIGS. 1A, 1B, 1C, and 1D). The primarily differences of the embodiments of FIGS. 1A, 1B, and 1C reside in the configuration of the respective illumination windows. Other differences for the embodiment of FIG. 1D will be mentioned below.

For all embodiments, the illumination window is formed along a predetermined length (indicated by arrow 42 in FIG. 1A) of the optical fiber major axis 28. The illumination window is located at a predetermined distance (indicated by arrow 44 in FIG. 1B) upstream from the optical fiber distal end 26.

As used herein, the "tip" of the illumination device is understood to include the distal end 24 of the optical fiber 24 and the illumination window. That is, the tip of the illumination device is understood to include at least the portion of the optical fiber which is upstream from the distal end 24 by a distance equal to the sum of the predetermined length (indicated by arrow 42 in FIG. 1A) and the predetermined distance (indicated by arrow 44 in FIG. 1B).

Figure 1A:
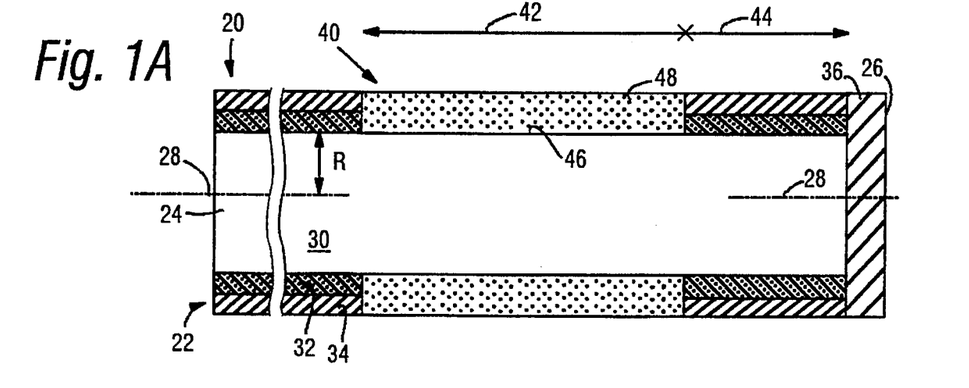
FIGS. 1A, 1B, 1C, and 1D are schematic cross-sectional views of illumination devices according to differing embodiments of the invention.

In the illuminator device 20 of embodiment of FIG. 1A, the cladding 32 and buffer 34 have been removed from the optical fiber 22 in the region of the illumination window 40. However, in contrast to the other embodiments described herein, the core 30 has not been etched or otherwise shaped. Accordingly, a circumferential contour 46 of the fiber core 30 has an essentially uniform cylindrical shape in the illumination window 40.

In the illumination window 40, the illumination device 20 has an optically scattering layer 48 circumferentially formed on the fiber core 30. As such, the optically scattering layer 48 has the shape of a hollow cylinder for the illumination device 20, with the exterior periphery of the scattering layer 48 being essentially flush with the exterior circumference of the fiber buffer 34.

Figure 1B:
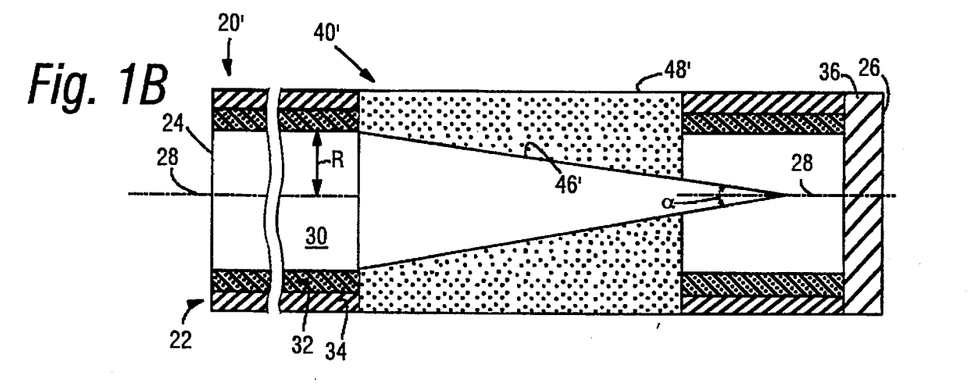

In the illumination window 40' of the illumination device 20', the fiber core 30 has been etched to assume the shape shown in FIG. 1B. In particular, the fiber core 30 has been etched (in accordance with procedures discussed below) so that a circumferential contour 46' of the core 30 has an essentially truncated or semi-conical shape. That is, the core 30 is etched so that radius of the core 30 (having the value R outside the window 40' and at the upstream end of the cone) tapers (i.e., decreases) toward the distal end 26 of the fiber. The radius of the core 30 does not form a perfect cone since, at the predetermined distance (indicated by arrow 44) from the distal end 26, the radius of the core immediately increases to assume again the non-window radius of the fiber. Thus, at the distal or upstream end of the illumination window 40', the core 30 has its smallest radius.

The semi-conical contour 46' of the core 30 in the window 40' has an interior planar angle α as shown in FIG. 1B. As used herein, "interior planar angle" is the extrapolated angle subtended by the intersection of the core 30 (assuming that the contour of the core were formed as a perfect cone) with a plane passing through the major axis 28 (e.g., the plane of the paper of FIG. 1B).

Figure 1C:
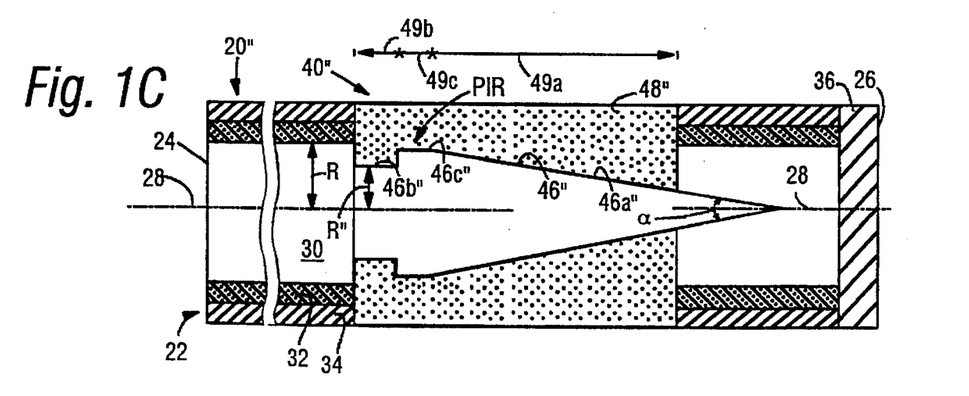

In the illumination window 40" of the illumination device 20", the core 30 has a contour 46" which is comprised of three segments 46a", 46b", and 46c". Along the first contour segment 46a" (e.g., along a distance denoted by arrow 49a), the core 30 has a truncated or semi-conical shape similar to that described above with reference to the embodiment of FIG. 1B (including a interior planar conical angle α). Along the second contour segment 46b" (e.g., along a distance denoted by arrow 49b), the core 30 has an essentially annular shape with a reduced radius R"<R. The reduced radius R" is generally 2 microns to 5 microns less than the radius R. The third contour segment 46c" is provided between the segments 46a" and 46b". Along the third contour segment 46c" (e.g., along a distance denoted by arrow 49c), the core 30 has an essentially annular shape and a radius greater than the radius R". The contour 46" of the illumination device 20" has a "modified conical" or "bi-tapered" shape.

As in the embodiment of FIG. 1A, the illumination windows 40' and 40" have a scattering layer (shown as 48' and 48", respectively) which is formed on the circumferential contour of the core 30 to surround radially the core 30. The scattering material is flush with the outer circumference of the buffer 34. The circumferential contours 46' and 46" of the core 30 represent an interface of the core 30 with the scattering layer.

Thus, the illumination windows 40' and 40" of the illumination devices 20' and 20", respectively, are configured so that an increase in the acceptance angle of ultraviolet light at the acceptance end 24 causes an increase at the distal end of the illumination window of ultraviolet light being coupled or irradiated out of the illumination window.

Figure 1D:
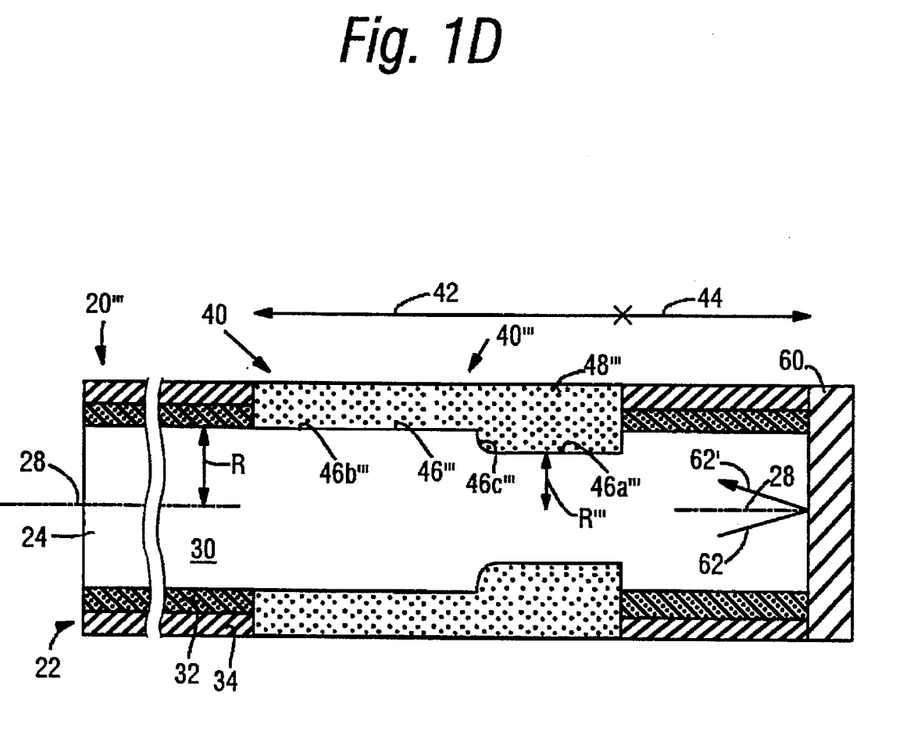

In the illumination window 40'" of the illumination device 20'" shown in FIG. 1D, the core 30 has a contour 46'" which is comprised of three segments 46a'", 46b'", and 46c'". Along the first contour segment 46a'" and the second contour segment 46b'", the core 30 has a cylindrical shape, However, the radius R''' of the core 30 along the first contour segment 46a''' is less than the radius R of the core along the second contour segment 46b'''. The third contour segment 36c''' serves as a short tapered ramp for bridging the first and second contour segments 46a''' and 46b''', respectively. The contour 46''' of the illumination device 20''' has a "ramped, two-radiused" shape. The manner of obtaining the contour 46''' of the illumination device 20''' will be understood from the ensuing discussion of the preparation of the devices of other embodiments, particularly with reference to the etching procedure.

As with the previously described embodiments, the illumination device 20''' of the embodiment of FIG. 1D has an optical scattering layer (i.e., the optical scattering layer 48''') formed over the portions of the core 30 which otherwise would be exposed. The optical scattering layer 48''' is formed to be flush with the buffer 34. In contrast to other embodiments, the percentage of $Al_2O_3$ in the admixture used to form the layer 48''' is only about 10%.

Unlike the other embodiments described herein, the illumination device 20''' of FIG. 1D does not have an opaque epoxy formed at its distal end. Rather, the illumination device 20''' has an aluminum mirror 60 secured (e.g., using chemical vapor deposition) to a polished distal end of the optical fiber 22. The aluminum mirror 60 serves to essentially totally reflect a ray incident thereon (such as ray 60) back toward the illumination window 40''' for further potential scattering from the illumination window 40'''.

In the illustrated embodiments hereof, the optical fiber 22 is a stop-index multimode fiber. The optical fiber 22 has a 300 μm diameter synthetic fused silica core. The cladding material 32 is also silica, and the buffer material 34 is preferably a polyimide buffer. Moreover, in the illustrated embodiments, the predetermined length (indicated by arrow 42) of the illumination window 40 is on the order of about 20 mm, and the predetermined upstream distance (indicated by arrow 44) of the window 40 from the fiber distal end is about 8 mm.

For each of the embodiments illustrated herein, the optically scattering material is an admixture of an optical (ultraviolet) epoxy and powdered $Al_2O_3$. The optical epoxy has an index of refraction on the order of about 1.56, while the powdered $Al_2O_3$ has an index of refraction on the order of about 1.63. As such, the scattering material has a different index of refraction than does the core 30.

Figure 6:
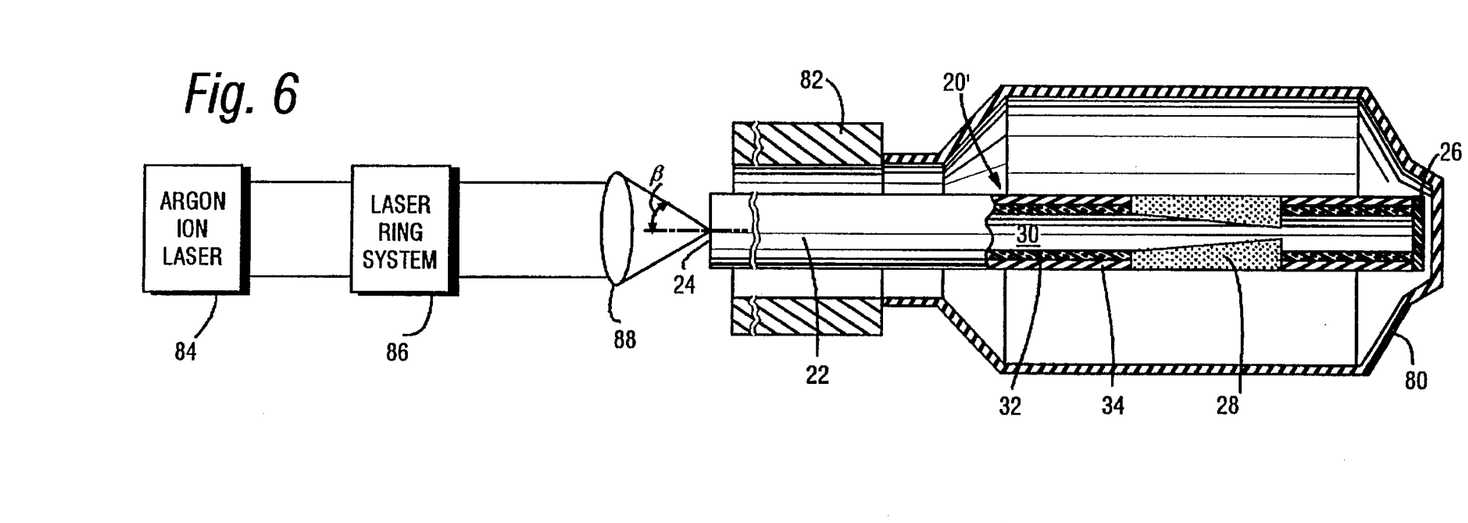
FIG. 6 is a schematic cross-sectional view showing the use of the illumination device of the embodiment of FIG. 1B within an angioplasty balloon and guided by a catheter.

FIG. 6 shows an assembly 78 for illuminating an angioplasty balloon 80 using the device 20' of the embodiment of FIG. 1B. As illustrated, the balloon 80 is a 3.5 mm×20 mm Mansfield™ balloon marketed by Boston Scientific Co. The balloon is guided by a 7F multipurpose catheter 82, such as the Super 7™ marketed by USCI Division CR Bard, Inc. The optical fiber 22 of the illumination device 20' terminates in a central diffusing tip within an inner lumen of the angioplasty balloon. The assembly 78 comprises an argon ion laser 84; a laser ring system 86; and, coupling optics (lens) 88. The laser ring system 86 is a Ti Sapphire Ring Laser System having a frequency doubling crystal for generating ultraviolet light. The laser ring system 86 is provided by a commercially available system known as The Coherent 899-01 Dye Ring Laser.

FIG. 6 shows that the beam of light converges on the acceptance end 24 of the optical fiber 22 at an acceptance angle β. As used herein, the term "acceptance angle" refers to the half angle of the incident axial cone (2β) in a uniform beam of light converging on the acceptance end 24 of the fiber 22 (i.e., the convergence angle of the input beam). The term "fiber acceptance angle", on the other hand, refers to the angle at which the fiber can accept light due to internal characteristics of the optical fiber.

METHODS OF PREPARATION: ETCHING

Figure 2A:
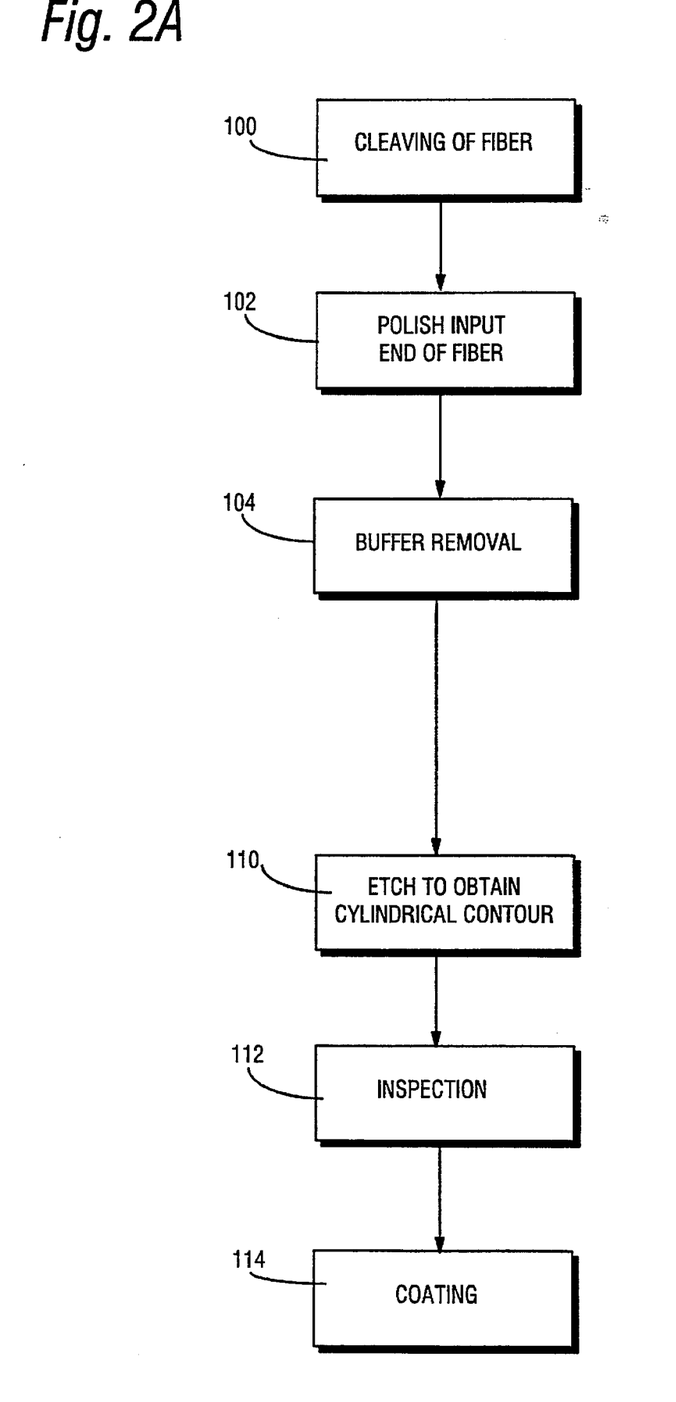
FIGS. 2A, 2B, and 2C are flowcharts showing steps involved in methods of preparation of illumination devices of FIGS. 1A, 1B, and 1C, respectively.

FIG. 2A shows steps involved in a method of preparation of the illuminator device of the embodiment of FIG. 1A. Methods of preparation of the illuminator devices of the embodiments of FIGS. 1B and 1C are described hereinafter with respect to the steps of FIGS. 2B and 2C, respectively.

In making the illumination device of the embodiment of FIG. 1A, at step 100 a piece of silica fiber is cut ("cleaved") to a length on the order of about 2 meters to 2.5 meters. Then, at step 102, a proximal or acceptance end 24 of the optical fiber is wet-polished using standard fiber polishing techniques to serve as an input end of the optical fiber 22.

At step 104 the protective polyimide buffer 34 is removed along the length of the fiber 22 which will serve as the illumination window 40. That is, approximately 20 mm of the protective buffer 34 is removed from the optical fiber 22, leaving about 10 mm of the buffer 34 between the illumination window 40 and the distal end 26 of the fiber 22. The protective buffer 34 is thermally removed using a stripper according to conventional techniques. The remainder of the protective buffer 34 (and underlying cladding 32) are left for ease of insertion inside the angioplasty balloon 80 and for enhancement of the bending strength of the optical fiber 20.

At step 110 the cylindrical contour 46 of the core 30 is exposed and obtained by etching away the cladding 32. During the etching step, the optical fiber is supported in a vertical position by attaching it to a vertical translator (such as that obtained from Line Tool, Inc.). The optical fiber 22 is then dipped into a solution of hydrofluoric acid (48%). The polyimide buffer 34 protects the cladding 32 and the core 30, so that only the cladding 32 in the region of the illumination window 40 is removed. The length of time for the etching of step 108 is determined by the thickness and nature of the cladding 32.

At step 112 the optical fiber 22, having the cladding 32 etched away from the region of the illumination window 40, is inspected (under an optical microscope) to ensure that the geometry of the illumination window 40 provides an essentially cylindrical contour 46 for the core 30.

At step 114 the exposed portion of core 30 in the region of the illumination window 40 is coated with the optical scattering material to form the optical scattering layer 40. Step 114 is described in more detail for all embodiments in connection with an ensuing description of the coating method of FIG. 5.

Figure 2B:
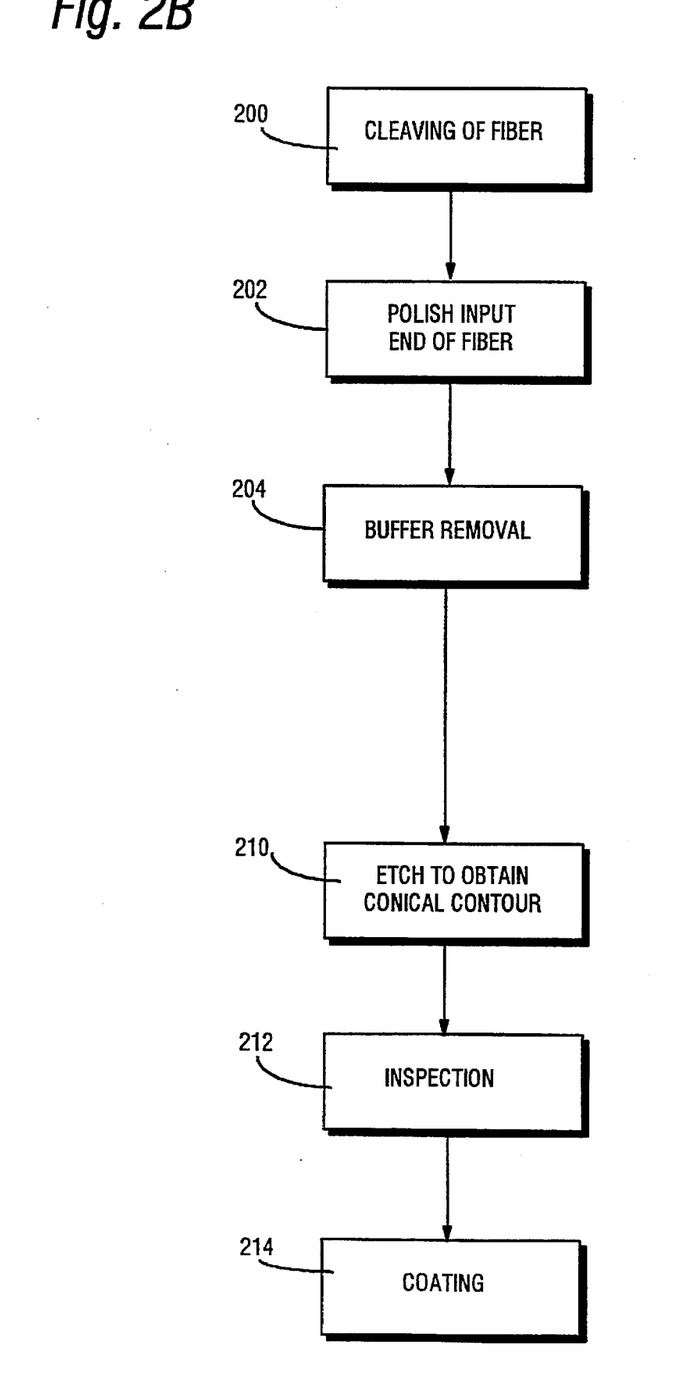

The steps of FIG. 2B illustrate a method for making the illumination device 20' of the embodiment of FIG. 1B. FIGS. 3A–3G show stages of preparation (corresponding to the numbered steps of FIG. 2B) of an illuminator device according to the embodiment of FIG. 1B.

Figure 3A:
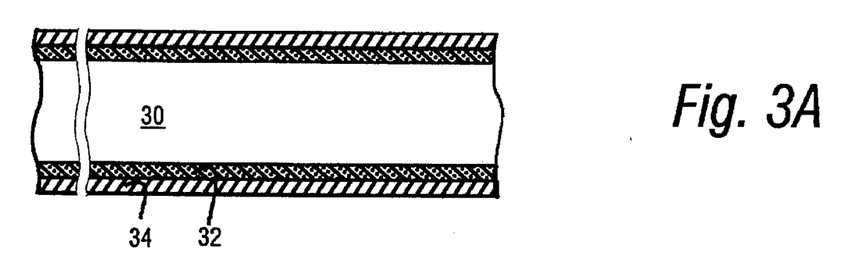
Figure 3B:
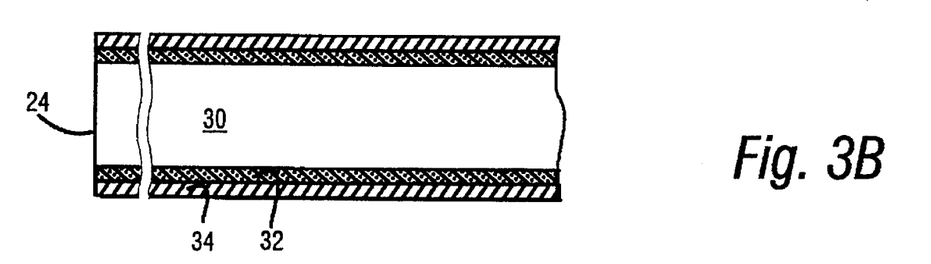
Figure 3C:
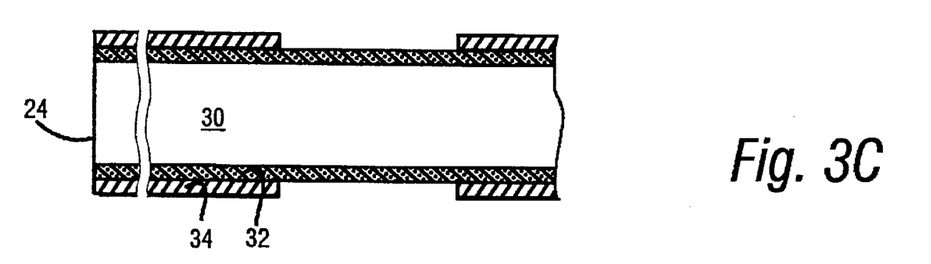

The method of FIG. 2B includes step 200 for cutting the optical fiber to length (see FIG. 3A); step 202 for polishing the acceptance end 24 of the fiber 22 (see FIG. 3B); and, step 204 for removing the protective polyimide buffer 34 (see FIG. 3C). The steps 200, 202, and 204 of the method of FIG. 2B are essentially identical to the respective steps 100, 102, and 104 of the method of FIG. 2A.

At step 210 the conical circumferential contour 46' is obtained by etching away both the cladding 32 and some of the core 30. As with the method of FIG. 1A, the optical fiber 22 with buffer 34 stripped therefrom is held by a vertical translator and dipped into the hydrofluoric acid (48%) bath. The optical fiber 22 is progressively (e.g., incrementally) lowered into the acid bath to obtain the essentially conical circumferential contour 46'. FIGS. 3D–3G show stages of the etching step 210 for progressive etching the cladding 32 and the core 30 in order to obtain the essentially conical circumferential contour 46'. At any point along the illumination window 40', the length of time that the optical fiber is exposed to the acid determines the extent of the etching, and accordingly the taper of the contour 46' of the core 30.

Figure 3D:
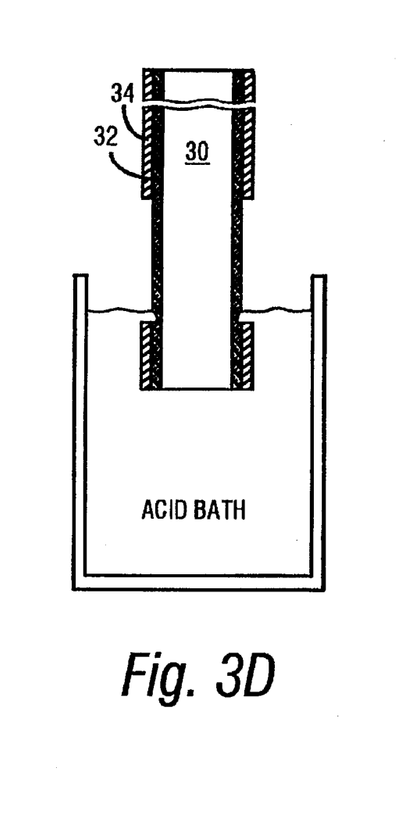
Figure 3E:
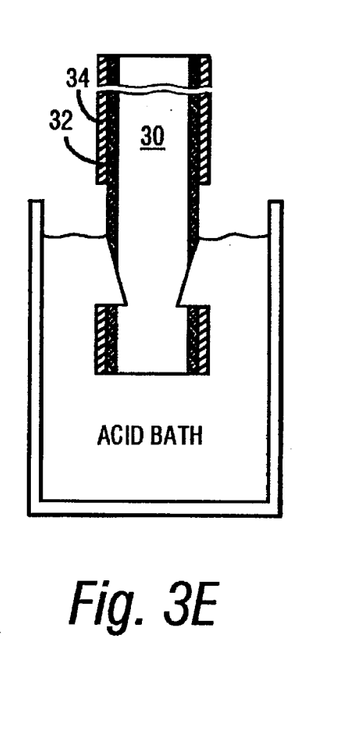
Figure 3F:
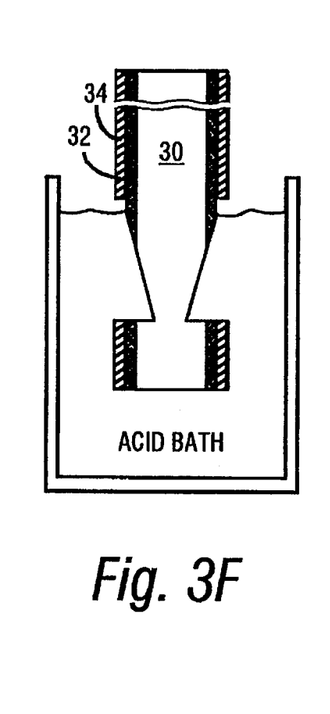
Figure 3G:
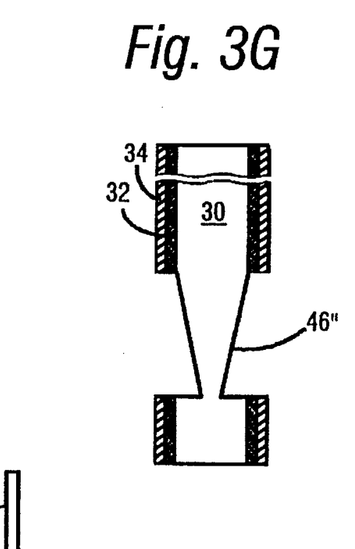

In conducting etching step 210, within a certain diameter range the etching rate is generally about 4 µm per minute. However, the etching rate is non-linear, since according to one mode it takes 4 minutes and 22 seconds to etch away 20 µm in diameter (a ratio of about 4.58 µm per minute) but 18 minutes to etch away 50 µm in diameter (a ratio of about 2.7 µm per minute). In view of the non-linearity, the etching rate has to be determined experimentally taking into consideration such factors as the quality of the optical fiber 22 and the constituency of the chemical (acid) bath. In the incremental etching of step 210 (roughly depicted by FIGS. 3D–3F), the etching occurs in increments of 0.4 mm, with each increment lasting about 20 seconds. It should, therefore, be understood that FIGS. 3D–3F show sequential, but not consecutive, stages of the etching step 210.

As in like manner with the method of preparation of the embodiment of FIG. 1A, at step 212 the tip of the illumination device 20' is inspected under a microscope. If the inspection indicates that a satisfactory circumferential contour has been obtained by the etching of step 210, at step 214 the etched regions are coated with the optical scattering material to form the scattering layer 28 of the illumination window 40'. The coating step 214 is described in further detail below with reference to FIG. 5.

Figure 2C:
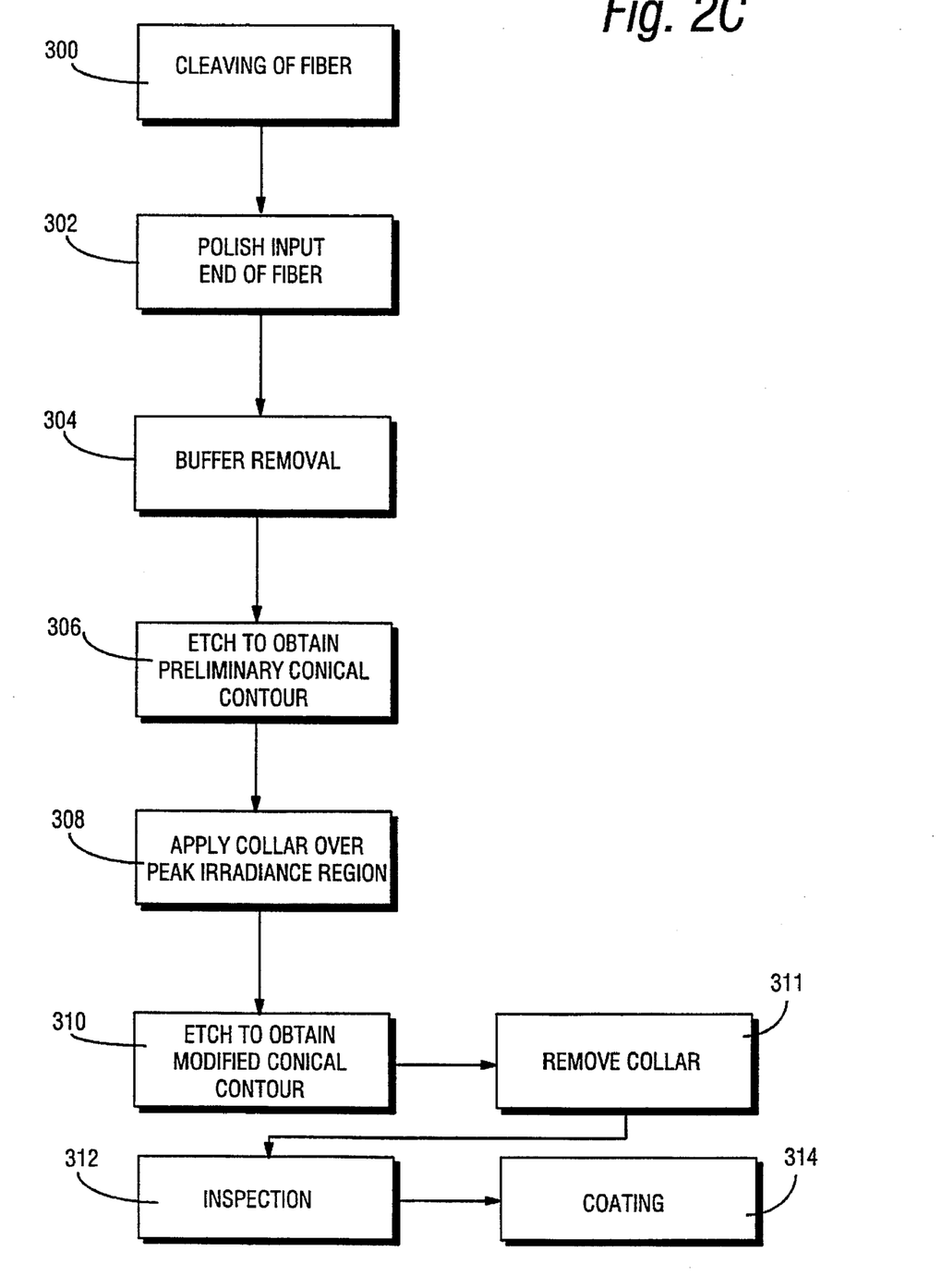

The steps of FIG. 2C illustrate a method for making the illumination device 20" of the embodiment of FIG. 1C. The method of FIG. 2C includes step 300 for cutting the optical fiber to length (similar to FIG. 3A); step 302 for polishing the acceptance end 24 of the fiber 22 (similar to FIG. 3B); and, step 304 for removing the protective polyimide buffer 34 (similar to FIG. 3C). The steps 300, 302, and 304 of the method of FIG. 2C are also essentially identical to the respective steps 100, 102, and 104 of the method of FIG. 2A.

Figure 4A:
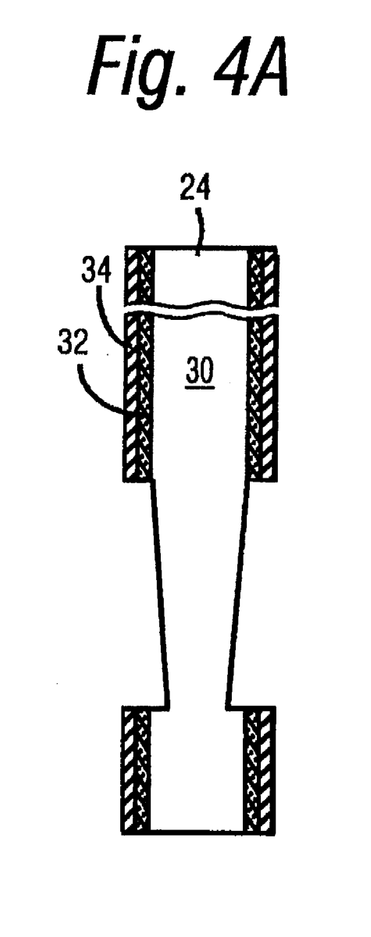

At step 306, the core 30 of the illumination device 20" is etched to acquire a preliminary conical contour as shown in FIG. 4A. Like with step 210 of the method described with reference to FIG. 2C, the etching step 310 involves an incremental lowering of the illumination device 20" into the acid bath. The etching of step 306 provides the conical contour that facilitates the contour segment 46a". The etching at step 306 must remove the cladding 32 in a peak irradiance region (PIR) hereinafter discussed.

Figure 4B:
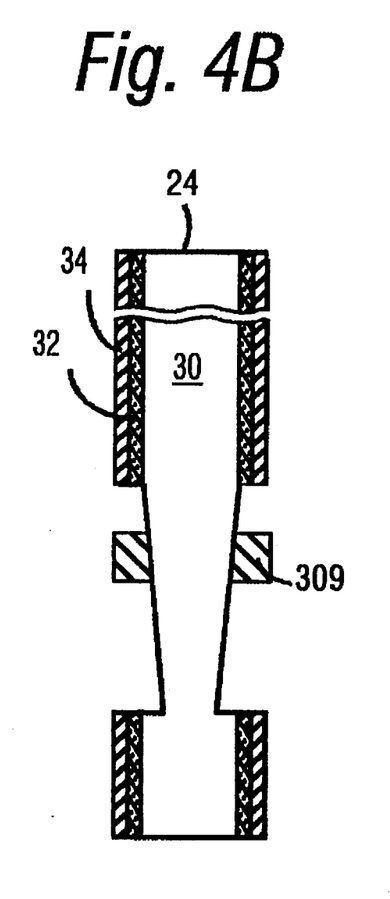

At step 308, a collar 309 is applied over the core 30 in a peak irradiance region PIR (see FIG. 4B). That is, the collar 309 is applied over a portion of the core 30 in the region of the illumination window 40" from which the maximum irradiance is expected to occur. The collar 309 can be formed using a polyimide tubing material, or be painted on the core 30 using a photoresist (such as Shipley photoresist 1350J), or an UV epoxy (such as LITETAK 376 mixed with $Al_2O_3$ powder (10:3).

The peak irradiance region PIR generally resides along the extent of the core 30 indicated by the arrow 49c in FIG. 1C. The extent of the peak irradiance region (i.e., the length depicted by arrow 49c) is about 3 mm. The distance separating the upstream end of the peak irradiance region PIR and the upstream-most portion of the illumination window 40" (e.g., the distance depicted by arrow 49b) is also about 3 mm. If desired, the precise location of the peak irradiance region PIR for the device 20" undergoing preparation can be determined at step 308 by temporarily applying an optical scattering coating mixture (described below) and determining the irradiance distribution at the tip of the illumination device 20" using conventional determination techniques.

Figure 4C:
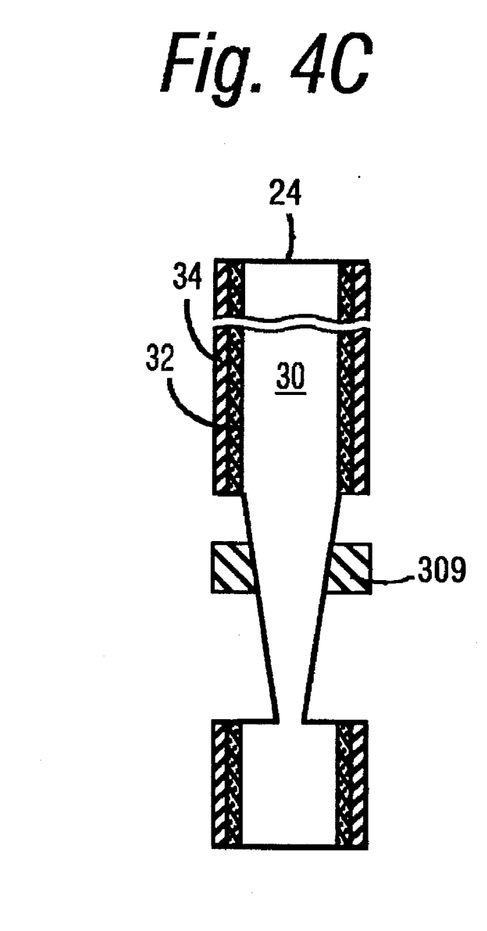

Then, at step 310, the entire tip of the illumination device 20" is again submerged into an acid bath, resulting in the modified conical or bi-tapered shape shown in FIG. 1C and FIG. 4C. The total submersion of the tip of the illumination device 20" into the chemical bath also etches an essentially ring-shaped notch at the upstream-most end of the illumination window 40", resulting (as seen in FIG. 1C) in the annular contour region 46b" hereinbefore described.

Upon completion of the etching step 310, the collar 309 is removed (at step 311). Thereafter, in like manner with the other methods described herein, the tip of the illumination device is inspected (step 132) and coated (step 314).

If desired, the light irradiance from the illumination device 20" can be preliminarily tested by dipping the etched tip into the optical scattering material coating mixture (described below). The irradiance distribution at the tip can then be measured using a known acceptance angle (e.g., 5°). If the irradiance distribution is not uniform, the coating mixture can be cleaned away with Acetone, and the etching step 310 can be repeated until a uniform irradiance is obtained.

METHODS OF PREPARATION: COATING

Figure 5:
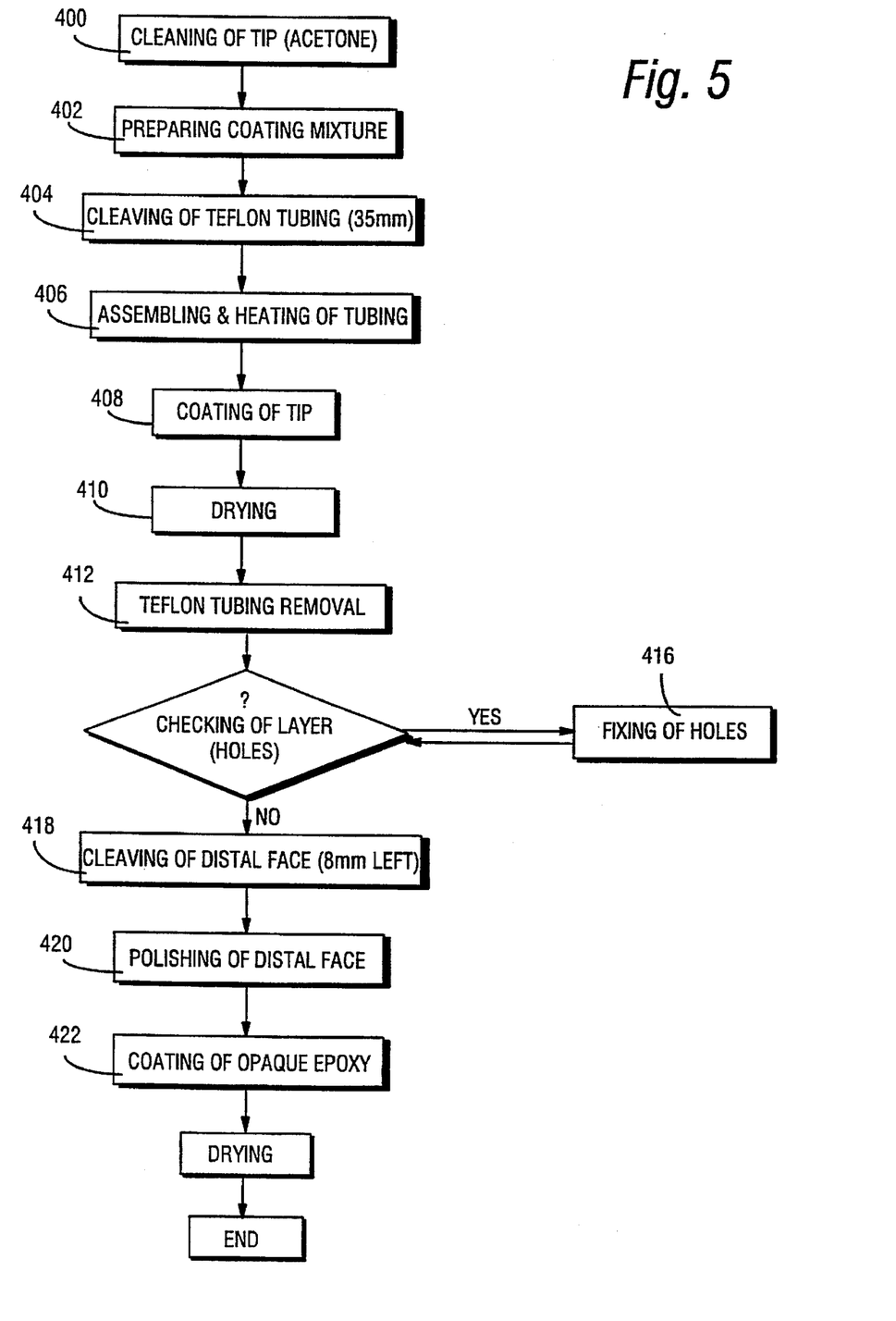
FIG. 5 is a flowchart showing steps involved in a coating process of the methods for preparing illumination devices of the invention.

FIG. 5 is a flowchart showing steps involved in a coating process for forming the optical scattering layer on the core 30 of the illumination devices of the invention. Although discussed below specifically with reference to the illumination device 20' of the embodiment of FIG. 1B, it should be understood that (with the exception of step 422 for the embodiment of FIG. 1D) the steps of FIG. 5 are applicable to coating procedures for each of the embodiments described herein. The steps of FIG. 5 thus serve as sub-steps for the step 114 of the method of FIG. 2A, as sub-steps for the step 214 of the method of FIG. 2B, and as sub-steps for the step 314 of the method of FIG. 2C.

At step 400, the illumination window 40' is thoroughly cleaned with Acetone. At step 402, a two-component coating mixture is prepared to be the optical scattering material. The coating mixture is prepared by thoroughly mixing an optical epoxy (such as EPO-TEK® 301-2) with a carefully weighted amount of $Al_2O_3$ powder. The optical epoxy and the $Al_2O_3$ powder are mixed in a weight ratio of 10:3. The $Al_2O_3$ powder is preferably commercial grade, the typical grain size being on the order of about 0.3 µm. The refractive index of the $Al_2O_3$ powder is 1.63.

At step 404 a 35 mm length segment is cut from a Teflon tube (28GA). At step 406, the tip of the illumination device is inserted into the segment of the Teflon tube. Moreover, at step 406 the segment of the Teflon tube containing the tip of the illumination device 20' is heated until the tube segment becomes straight. In one mode of the invention, the heating is accomplished using a hot-air gun.

At step 408 the coating mixture is actually applied to the tip of the illumination device 20' for producing the optical scattering layer 28'. The tip of the illumination device 20' (having the coating mixture applied thereon) is then run through the interior of the Teflon tube segment. The Teflon tube segment is then moved back and forth over the tip of the illumination device 20'. The tip of the illumination device 20' can be repeatedly run through the Teflon tube segment as needed. The filling of the etched portion of the cladding 32 and core 30 with the optical scattering mixture occurs as the Teflon tube is moved back and forth along the tip of the illumination device 20'. The space between the inside wall of the Teflon tube and the tip of the illumination device 20' is filled with the coating mixture (the optical scattering material), particularly the etched portion of the illumination window. Should any small air bubbles occur in the coating mixture, the air bubbles are removed by warming the coating mixture with a hotplate or a hot-air gun.

At step 410 the tip of the illumination device 20' is allowed to dry in a vertical position in a warm environment (about 75°). After the drying step 410, the Teflon tube segment is removed thermally (step 412). During the removal step 410, a metal block is positioned on a hotplate and warmed to above 100° C. The Teflon tube segment is then put in contact with the metal block, and the Teflon tube segment is removed as soon as possible with tweezers.

On occasion there may be small holes in the optical scattering layer 28' which results from the execution of the foregoing steps. Such small holes may result from the differences in tension on the layer surface during drying. Should such holes be detected (at step 414), the holes can easily be filed with the coating mixture at step 416.

At step 418 the distal end 26 of the optical fiber 22 is cleaved, leaving 8 mm of buffer 34 and cladding 32 between the distal end and the downstream-most edge of the illumination window 40'. At step 420 the distal end 26 of the optical fiber 22 is polished. At step 422 the distal end 26 is coated with an optically opaque epoxy 36 (e.g., EPO-TEK® 320) whose transmission is less than 0.0001% at 300 nm to 1 micron. The optically opaque epoxy 36 stops the transmitted light in the forward direction (i.e., the downstream direction) so as to ensure that the closed end of the balloon 80 receives minimal or no direct laser exposure (see FIG. 6).

In lieu of step 422, for the embodiment of FIG. 1D a reflective surface (such as aluminum mirror 60) is formed on the distal end 26 of the optical fiber 22. As mentioned above, the reflective surface can be formed by chemical vapor deposition (CVD) techniques.

At step 424 the illumination device 20' is dried. The coating process then terminates as indicated by step 426.

OPERATION

The optical behavior of the illumination devices of the present invention depend upon several factors. A first of the factors is the geometry of the illumination window, and particularly the circumferential contour of the core 30. Other factors are the acceptance angle of the incident beam; the refractive index of the core, the refractive index of the optical scattering layer, and the concentration of the optical scattering power (e.g., the $Al_2O_3$) in the optical scattering layer.

Figure 7A:
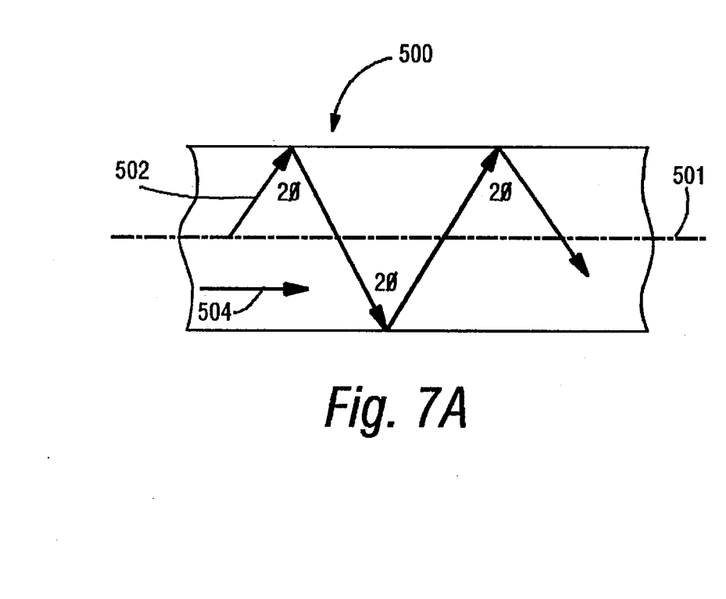
FIGS. 7A is a schematic drawings illustrating rays internally reflected in prior art illuminating devices.
Figure 7B:
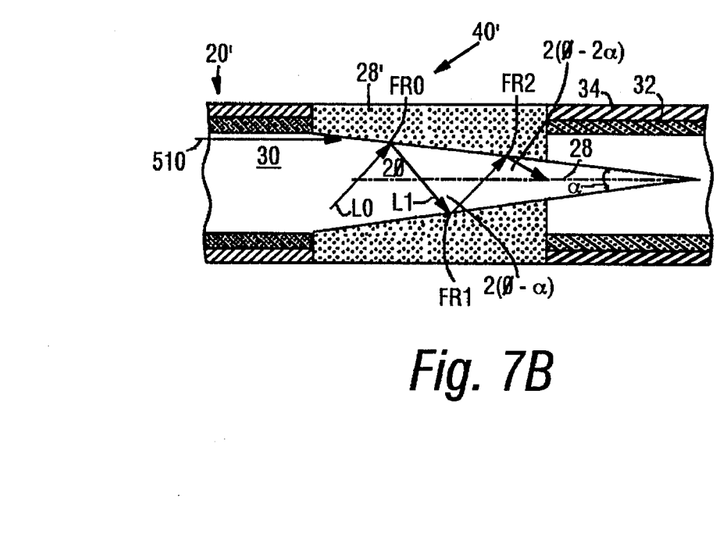
FIGS. 7B is a schematic drawings illustrating rays internally reflected in illuminating devices of embodiments of the invention.

FIG. 7B illustrates advantages of the illumination device 20' whose core 30 has an essentially conical circumferential geometry in the region of the illumination window 40'. In the illumination window 40' wherein the buffer 34 and cladding 32 have been removed (and the optical scattering layer 28' applied), the total internal reflection properties of the optical fiber 22 are lost and an anti-guiding situation occurs. Light (such as ray L0) propagating in the lower refractive index core 30 is redistributed at each Fresnel reflection (FR0, FR1, FR2) at the interface between the core 30 and the optical scattering layer 28' (which has a higher index of refraction). Depending on the angle of incidence, at each Fresnel reflection some of the light is refracted into the scattering layer 28', and a fraction is internally reflected (e.g., ray L1) to the other side of the core 30 where (as at FR1, for example), it is redistributed again at the core-scattering layer interface. In this manner, each ray L0 generates an increasing number of subrays of ever-decreasing amplitude as it propagates along the tip of the illumination device 20'. Therefore, the radiation is refracted into the scattering layer 28' and then scattered out of the illumination window 40' in a sequential manner. As explained below, the anti-guiding geometry of the conically tapered contoured core 30 significantly redistributes the input radiation along the illumination window 40'.

In the above regard, contrasts between the illumination device 20' of the present invention (depicted in FIG. 7B) are understood with reference to FIG. 7A. FIG. 7A is a schematic diagram illustrating ray propagation and reflection in a prior art cylindrical illumination device 500. In such prior art cylindrical illumination devices, only the rays (such as ray 502) at angles with respect to the optical fiber axis 501 could be refracted from the optical fiber core. In other words, a ray parallel to the optical fiber axis 501, such as ray 504, would not be refracted and hence would not substantially contribute to irradiance. Moreover, for the prior art cylindrical illumination device 500, the angles of incidence $2\phi$ remain constant.

On the other hand, the illumination device 20', as depicted in FIG. 7B, results in reflection and refraction even for rays (such as ray 510) which are parallel to the major axis 28. The reflection and refraction of ray 510 is occasioned by the fact that ray 510 strikes interface depicted by the conical circumferential contour 46' at an angle of incidence. The conical circumferential contour 46' of the core 30 thus contributes to the reflection and refraction of rays parallel to the major axis 28.

Moreover, with the illumination device 20' depicted in FIG. 7B, the incident angle between the ray and the normal to the core-layer interface will be decreased by the amount $\alpha$ after each reflection, where $\alpha$ is the aforedescribed interior planar angle $\alpha$ shown in FIG. 1B. That is, an internally reflected ray which has a first angle of incidence $\theta_i$ at a first point of reflection along the illumination window and a plurality N of further points of subsequent reflection along the predetermined length, will have an interior angle of total reflection of $2(\theta_i-(N-1)\alpha)$ for the subsequent points of internal reflection in the illumination window. In view of the conical circumferential contour 46' of the core 30, and the sequential reduction of the incident angle, more light is refracted from the core 30.

The foregoing discussion equally applies with respect to the conically tapered contour segment 46a" of the illumination device 20" of the embodiment of FIG. 1C. Moreover, not only can more rays be refracted from the core 30, but also more light can be coupled out of the core 30 at the beginning of the illumination window 40" (i.e., along the extent indicated by arrow 49b shown in FIG. 1C) in view of the recessed contour segment 46b". The enhanced coupling of light from the beginning of the illumination window 40" is in contrast to prior art devices, wherein the light irradiated from the first one to two mm is generally considerably lower than the peak irradiance.

Concerning the factor of acceptance angle, it is well known that fiber optical delivery of laser light is associated with Gaussian beam optics. E. Hecht and A. Zajak, *Optics*, Addison-Wesley, Reading, N.H. 1979. The irradiance distribution of the laser beam emitted from a multimode fiber is usually assumed to have a Gaussian angular distribution. See W. Siegmand, "Fiber Optics" in *Handbook of Optics*, W. Driscoll and W. Vaughan, Editors, McGraw-Hill, New York, 1978. Because this Gaussian distribution is related to which fiber modes are excited, considerable variation in displacement of the irradiance peak can be achieved by varying the acceptance angle β. Small acceptance angles will excite primarily low-order modes and move the irradiance peak in a direction towards the distal end 26 of the device 20 (i.e., downstream), while larger acceptance angles can excite both low and high-order fiber modes and move the irradiance peak in a direction toward the acceptance end 24 (i.e., upstream).

Thus, the present invention provides methods for obtaining optimum structure when given an expected acceptance criteria. That is, given a particular acceptance criteria, the taper of the circumferential contour of the core 30 (e.g., the interior planar angle α) can be optimally determined to provide uniform cylindrical irradiation. The expected light acceptance criteria can be the acceptance angle upon which light is incident at an acceptance end of the optical fiber; the fiber acceptance angle of the optical fiber; or a combination thereof.

Concerning the factors of the refractive index of the core 30 and the optical scattering layer, the internal reflectance will increase with increasing difference between the refractive indices of the core 30 and the optical scattering layer. This is understood with reference to Equation 20a of Max Born and Emil Wolf, *Principles of Optics*, Pergamo Press 1970. Thus, with increased difference between the refractive indices, more light will be reflected toward the distal end 26 of the illumination device.

The effect of powder concentration of the optical scattering layer is a complex phenomena. Usually, with increasing powder concentration, the scattering coefficient of the scattering layer will increase and the light will be scattered out of the illumination window more uniformly than without the powder. This appears particularly true when the particles of the powder are widely separated, but may not hold true when the particle separations are less than or comparable to the wavelength of the light. In general, the irradiance dependence on the powder concentration is thought to be similar to that of the acceptance angle. See Lnnaart Hasselgren, Sncila Galt, and Sverker Hard, "Diffusive Optical Fiber Ends For Photodynamic: Manufacturtherapyre and Analysis," *Applied Optics*, Vol. 29, No. 30, pp. 4481–4488, 1990.

While the invention has been particularly shown and described with reference to the preferred embodiments thereof, it will be understood by those skilled in the art that various alterations in form and detail may be made therein without departing from the spirit and scope of the invention.

We claim:

1. A device for delivering ultraviolet light to an in vivo treatment site, the device comprising:

an optical fiber having a fiber core and a circumferential covering, the fiber core having a major axis, the device having the covering removed from the fiber core along the predetermined length thereof;

a circumferential contour of the core being shaped along the predetermined length whereby a ray travelling in the core parallel to the major axis makes an angle of incidence with the circumferential contour of the core along the predetermined length thereof; and an optical scattering material radially surrounding the core along the predetermined length, the optical scattering material having a different index of refraction than the core.

2. The device of claim 1, wherein the core has an essentially conical shape along at least a portion of the predetermined length.

3. The device of claim 1, wherein at least a portion of the core has the shape of a truncated cone along the predetermined length, the truncated cone having an internal planar conical angle α, wherein an internally reflected ray has a first angle of incidence $\theta_i$ at a first point of reflection along the predetermined length with respect to the circumferential contour and a plurality N of further points of subsequent reflection along the predetermined length, and wherein for the subsequent points of internal reflection the ray has an interior angle of total reflection of $2(\theta_i-(N-1)\alpha)$.

4. The device of claim 1, wherein along the predetermined length the core has at least two segments, a first of the segments having an essentially conical shape and a second of the segments having an annular shape, a radius of the second shape being smaller than a largest radius for the first segment.

5. The device of claim 1, wherein the light delivered to the in vivo treatment site is ultraviolet light.

6. A device for delivering ultraviolet light to an in vivo treatment site, the device comprising:

an optical fiber having a fiber core and a circumferential covering, the device having the covering removed from the fiber core along the predetermined length thereof;

a circumferential contour of the core being shaped along the predetermined length whereby, for an internally reflected ray travelling in the core, the internally reflected ray has differing angles of incidences along the predetermined length with respect to the circumferential contour; and an optical scattering material radially surrounding the core along the predetermined length, the optical scattering material having a different index of refraction than the core.

7. The device of claim 6, wherein at least a portion of the core has the shape of a truncated cone along the predetermined length, the truncated cone having an internal planar conical angle α, wherein an internally reflected ray has a first angle of incidence $\theta_i$ at a first point of reflection along the predetermined length with respect to the circumferential contour and a plurality N of further points of subsequent reflection along the predetermined length, and wherein for the subsequent points of internal reflection the ray has an interior angle of total reflection of $2(\theta_i-(N-1)\alpha)$.

8. The device of claim 6, wherein along the predetermined length the core has at least two segments, a first of the segments having an essentially conical shape and a second of the segments having an annular shape, a radius of the second shape being smaller than a largest radius for the first segment.

9. The device of claim 6, wherein the predetermined length is spaced away from a distal end of the optical fiber, and wherein the distal end of the optical fiber is optically opaque.

10. The device of claim 6, wherein the optical scattering material comprises an ultraviolet epoxy and an optical scattering powder.

11. The device of claim 10, wherein the optical scattering powder is $Al_2O_3$.

12. The device of claim 6, wherein the core has an essentially conical shape along at least a portion of the predetermined length.

13. The device of claim 6, wherein the light delivered to the in vivo treatment site is ultraviolet light.

14. A device for delivering ultraviolet light to an in vivo treatment site, the device comprising:
an optical fiber having a fiber core and a circumferential covering, the device having the covering removed from the fiber core along a predetermined length thereof;
a circumferential contour of the core having an essentially conical shape along at least a portion of the predetermined length; and
an optical scattering material radially surrounding the core along the predetermined length, the optical scattering material having a different index of refraction than the core.

15. The device of claim 14, wherein the predetermined length is spaced away from a distal end of the optical fiber, and wherein the distal end of the optical fiber is optically opaque.

16. The device of claim 14, wherein the optical scattering material comprises an ultraviolet epoxy and an optically scattering powder.

17. The device of claim 16, wherein the optically scattering powder is $Al_2O_3$.

18. The device of claim 14, wherein at least a portion of the core has the shape of a truncated cone along the predetermined length, the truncated cone having an internal planar conical angle $\alpha$, wherein an internally reflected ray has a first angle of incidence $\theta_i$ at a first point of reflection along the predetermined length with respect to the circumferential contour and a plurality N of further points of subsequent reflection along the predetermined length, and wherein for the subsequent points of internal reflection the ray has an interior angle of total reflection of $2(\theta_i-(N-1)\alpha)$.

19. The device of claim 14, wherein along the predetermined length the core has two segments, a first of the segments having an essentially conical shape and a second of the segments having an annular shape, a radius of the second shape being smaller than a largest radius for the first segment.

20. The device of claim 14 wherein the light delivered to the in vivo treatment site is ultraviolet light.

21. A method of forming a device for delivering ultraviolet light to an in vivo treatment site, the method comprising:
removing a covering from an optical fiber core to expose the core along a predetermined length thereof;
contouring the core along the predetermined length to form an optical window in accordance with an expected light acceptance criteria; and
surrounding the core along the predetermined length with an optical scattering material.

22. The method of claim 19, wherein the step of contouring the core comprises etching the core along the predetermined length whereby the core has a predetermined circumferential contour along the predetermined length.

23. The method of claim 21, wherein the expected light acceptance criteria is the acceptance angle upon which light is incident at an acceptance end of the optical fiber.

24. The method of claim 21, wherein the expected light acceptance criteria is the fiber acceptance angle of the optical fiber.

25. The method of claim 21, wherein the light delivered to the in vivo treatment site is ultraviolet light.

26. A method of forming a device for delivering ultraviolet light to an in vivo treatment site, the method comprising:
removing a covering from an optical fiber core to expose the core along a predetermined length thereof;
shaping a circumferential contour of the core along the predetermined length whereby, for an internally reflected ray travelling in the core, the internally reflected ray has differing angles of incidences along the predetermined length with respect to the circumferential contour; and
surrounding the core along the predetermined length with an optical scattering material.

27. The method of claim 26, wherein the core is shaped to have an essentially conical shape along at least a portion of the predetermined length.

28. The method of claim 26, wherein the core is shaped so that at least a portion of the core has the shape of a truncated cone along the predetermined length, the truncated cone having an internal planar conical angle $\alpha$, wherein an internally reflected ray has a first angle of incidence $\theta_i$ at a first point of reflection along the predetermined length with respect to the circumferential contour and a plurality N of further points of subsequent reflection along the predetermined length, and wherein for the subsequent points of internal reflection the ray has an interior angle of total reflection of $2(\theta_i-(N-1)\alpha)$.

29. The method of claim 26, wherein along the predetermined length the core is shaped to have at least two segments, a first of the segments having an essentially conical shape and a second of the segments having an annular shape, a radius of the second shape being smaller than a largest radius for the first segment.

30. The method of claim 26, wherein the light delivered to the in vivo treatment site is ultraviolet light.

31. A device for delivering ultraviolet light to an in vivo treatment site, the device comprising:
an optical fiber having a fiber core and a circumferential covering, the fiber core having a major axis, and acceptance end upon which light is incident, and a distal end, the device having the covering removed from the fiber core along the predetermined length thereof and an optical scattering material radially surrounding the core along the predetermined length to form an illumination window, the distal end of the optical fiber having a reflective surface formed thereon to reflect light incident from the acceptance end back toward the illumination window.

32. The device of claim 31, wherein the light delivered in vivo treatment site is ultraviolet light.

33. A method of forming a device for delivering ultraviolet light to an in vivo treatment site, the method comprising:
removing a covering from an optical fiber core to expose the core along a predetermined length thereof;
shaping a circumferential contour of the core along the predetermined length whereby a ray travelling in the core parallel to a major axis makes an angle of incidence with the circumferential contour of the core along the predetermined length thereof;
surrounding the core along the predetermined length with an optical scattering material.

34. The method of claim 33, wherein the core is shaped to have an essentially conical shape along at least a portion of the predetermined length.

35. The method of claim 33, wherein along the predetermined length the core is shaped to have at least two segments, a first of the segments having an essentially conical shape and a second of the segments having an annular shape, a radius of the second shape being smaller than a largest radius for the first segment.

36. The method of claim 33, wherein the light delivered to the in vivo treatment site is ultraviolet light.

37. A device for delivering ultraviolet light to an in vivo treatment site, the device comprising:

an optical fiber having a fiber core and a circumferential covering, the fiber core having the covering removed from the fiber core along a predetermined length thereof;

the core being shaped to have differing radii along the predetermined length;

an optical scattering material radially surrounding the core along the predetermined length.

38. A device for delivering ultraviolet light to an in vivo treatment site, the device comprising:

an optical fiber having a fiber core and a circumferential covering, the fiber core having the covering removed from the fiber core along a predetermined length thereof;

the core having a multitapered contour along the predetermined length;

an optical scattering material radially surrounding the core along the predetermined length.

39. A device for delivering ultraviolet light to an in vivo treatment site, the device comprising:

an optical fiber having a fiber core and a circumferential covering, the fiber core having the covering removed from the fiber core along a predetermined length;

the core having a first contour segment along a first portion of the predetermined length and a second contour segment along a second portion of the predetermined length;

an optical scattering material radially surrounding the core along the predetermined length.

40. The device of claim 39, wherein the second contour segment is shaped so that more light is coupled out of the core at the second portion of the predetermined length than would be the case if the contour of the predetermined length were uniform.

41. The device of claim 40, wherein the first portion is along a distal portion of the predetermined length and the second portion is along a proximal portion of the predetermined length.

42. A device for delivering ultraviolet light to an in vivo treatment site, the device comprising:

an optical fiber having a fiber core and a circumferential covering, the fiber core having the covering removed from the fiber core along an illumination window, the illumination window being spaced away from a distal end of the optical fiber whereby the circumferential covering extends over the distal end of the optical fiber;

an essentially totally reflective mirror situated at a distal end of the optical fiber to reflect light toward the illumination window;

an optical scattering material radially surrounding the core along the illumination window.

* * * * *